United States Patent [19]
Alonso

[11] Patent Number: 5,637,791
[45] Date of Patent: Jun. 10, 1997

[54] METHOD AND APPARATUS FOR MEASURING VAPOR PRESSURE OF MULTICOMPONENT LIQUIDS

[76] Inventor: Joey G. Alonso, 3400 Princeton Way, Anchorage, Ak. 99508

[21] Appl. No.: 325,491

[22] Filed: Oct. 19, 1994

[51] Int. Cl.⁶ .................................................. G01N 13/00
[52] U.S. Cl. ............................................................ 73/64.45
[58] Field of Search ........................... 73/61.78, 64.45, 73/64.46

[56] References Cited

U.S. PATENT DOCUMENTS 3,056,282  10/1962  Boyd, Jr. ........................ 73/64.45 X
4,905,505   3/1990  Reed .................................. 73/64.46

*Primary Examiner*—Michael Brock

[57] ABSTRACT

An online vapor pressure analyzer that determines continuously and not in batch mode, the vapor pressure of a sidestream sample composed of a single compound liquid having a single vapor pressure or a mixture of liquid compounds having different vapor pressures. It determines the highest pressure of the liquid in a given temperature at which the lightest component starts to flash, such pressure being the vapor pressure of the liquid at that temperature. The sidestream sample is pass through the analyzer and then returned to the process line. The analyzer is comprised of an upstream aeration or density measurement means, a pressure reducing means such as capillary tubing to reduce the pressure to the vapor pressure of the liquid without creating pressure recovery and promote flashing at the true vapor pressure by fluid shear, a downstream aeration or density measurement means, and instrumentation means to detect vapor pressure, temperature and minimum aeration or density change that signifies flashing of the lightest component at the vapor pressure of the liquid. A flow regulator controls amount of sample admitted and therefore controls the pressure drop across the capillary tubing. A pumps returns the sample to the process line.

8 Claims, 1 Drawing Sheet

METHOD AND APPARATUS FOR MEASURING VAPOR PRESSURE OF MULTICOMPONENT LIQUIDS

BACKGROUND OF THE INVENTION

1. Field of the Invention

The present invention relates to the determination of the vapor pressure of a single compound liquid having a single vapor pressure or a mixture of liquid compounds having different vapor pressures. An example of a single compound liquid is propane; an example of a liquid mixture composed of different compounds with different vapor pressures is crude oil. The present invention determines the highest pressure of the liquid in a given temperature at which the lightest component starts to flash, such pressure being the vapor pressure of the liquid at that temperature.

2. Prior Art

The determination of the correct vapor pressure in pure liquids or liquid mixtures is very important for the processing of such liquids. One reason for measuring vapor pressure of liquids is to assure that the available net positive suction head of a pump is not less than the required net positive suction head to prevent cavitation and pump damage. Another reason for measuring vapor pressure is to determine how much vapor would escape through vents in storage tanks. Still another very important use of vapor pressure analyzers is to determine the flash point of flammable liquids to determine how safely they can be handled.

Present devices exist to measure vapor pressure of liquids such as Boyd's and Hills' apparatus, U.S. Pat. No. 3,056,282 which is composed of a venturi nozzle where the liquid is passed through. The pressure decreases as the liquid passes through the throat of the nozzle causing it to flash at some pressure existing at the throat which is claimed to be the vapor pressure of the liquid. For single compound liquids this may be accurate but only when not all of the liquid has flashed. Since there is no control on the amount of liquid that is flashed or on how much to decrease the pressure of the sample to reach the vapor pressure, accuracy cannot be ascertained. For multi compound mixtures it is even worse because the pressure should only be dropped enough for the lightest fraction to begin to flash. In a venturi the pressure will continue to decrease after initial flashing because there is no controller to stop further expansion once initial flashing is obtained. The liquid mixture will continue to flash even after all the lightest fraction has flashed because flashing will only stop when equilibrium pressure is reached.

Other devices that attempt to measure multi component liquids having different boiling points do so either using the same principle as for the single component liquid or relies on a sampling technique that analyzes the sample in batches such as Reed's apparatus in U.S. Pat. No. 5,172,586. In a batch sampling technique, the sample of the multi component liquid is accumulated in a cylinder. It is then expanded in steps in the chamber and the pressure is monitored. Since the fluid is analyzed in batches instead of continuously, the vapor pressure of the flowing liquid is not measured while the sample is still being analyzed. Also, this device waits for the sample to stabilize which can increase the length of the sampling interval and therefore the device cannot monitor changes in vapor pressure occurring in the system during the analysis interval. Sampling time is 30 to 300 seconds. Also, the space occupied by the liquid is expanded by 20% initially which drops the pressure in the chamber below the vapor pressure of the sample. This means that it cannot be ascertained what the vapor pressure of the sample is because at equilibrium conditions with 120% of initial volume, all the lightest fraction may already have flashed and the equilibrium pressure is then at a lower pressure than it would have been if the sample were only expanded to a point as to initially flash the lightest fraction. Moreover, linear interpolation will not likely yield the true vapor pressure. Another disadvantage of these prior arts is that accuracy can be affected by dirt or solid accumulation inside the sampling chamber. After a certain interval the parts have to be taken off line, dismantled and cleaned.

SUMMARY OF THE INVENTION

Whatever the merits, features and advantages of the above cited references, none of them achieves or fulfills the purposes of the present invention which is to continuously and accurately measure the vapor pressure of multi-component liquid mixtures such as crude oil or just single component liquids. It is also the object of the present invention to provide a device which is reliable, rugged and relatively inexpensive. Another object of the invention is to provide a device that has no moving parts which can affect the accurate measurement of vapor pressure when worn off, plugged or when seals fail.

The foregoing objectives can be accomplished by providing a vapor pressure analyzer that consists of the following: an inlet conduit, an inlet filter to remove solid particles that might plug the pressure reduction device, an upstream density or aeration measurement device, a pressure reduction device such as a capillary tubing that smoothly reduces the pressure of the sample to the saturation pressure of the lightest component without any pressure recovery such as would occur if a regular pressure control valve were used, a downstream density or aeration measurement device, a vapor pressure measuring means and temperature measuring means in the same location, a flow controller to control the amount of sample being admitted to the vapor pressure analyzer and auxiliary equipment such as heater and cooler to maintain a desired sample temperature and flow tubing interconnecting the above mentioned devices. The aeration measurement device detects bubbles generated when the liquid starts effervescing upon reaching the saturation pressure of the component having the highest vapor pressure. The pressure at which the initial effervescence is detected by the aeration measurement device is the vapor pressure of the liquid. The density measurement device accomplishes the same result as the aeration measurement device by determining the change in density of the liquid as it starts to flash. Since the difference in density of liquid and gas is large, a very small effervescence or flashing resulting from reaching the saturation pressure of the lightest fraction will translate into a relatively large decrease in density. The pressure at which this particular change in density is initially detected is the vapor pressure of the liquid at the given temperature.

DETAILED DESCRIPTION OF THE INVENTION

Figure 1:
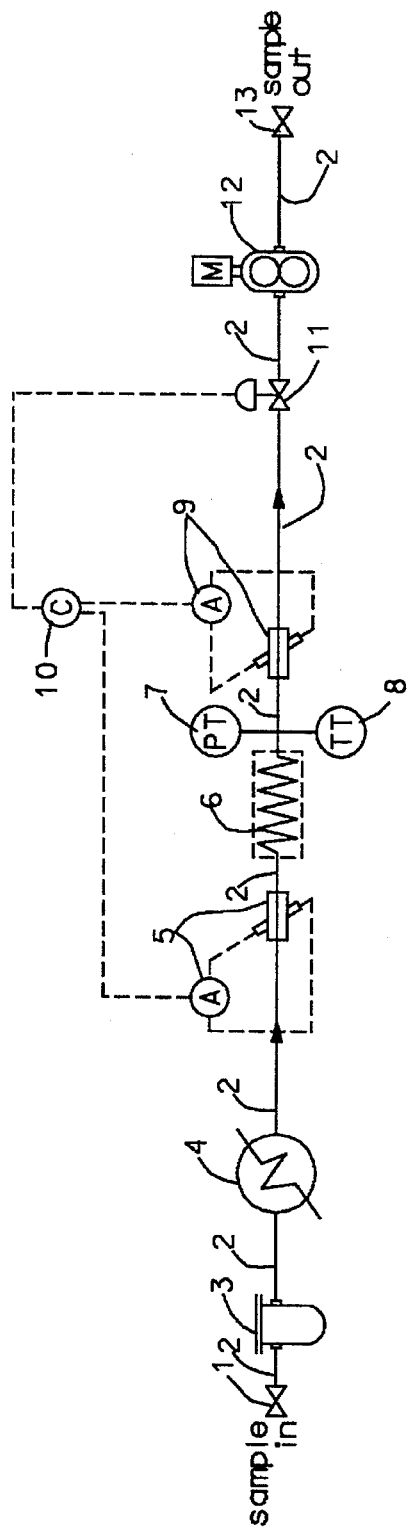
FIG. 1 is a schematic representation of the vapor pressure measurement apparatus according to the present invention showing aeration measurement means for detecting flashing or formation of bubbles.

The major feature of the present invention, the accurate and continuous determination of vapor pressure of a single or multicomponent liquid, is achieved by continuously extracting and analyzing a side stream sample of the liquid whose vapor pressure is being determined. This invention is an on-line analyzer that performs continuous analysis of the sample and is not a batch type analyzer. One benefit of such an on-line device is the continuous monitoring of the vapor pressure in a process which in turn allows quick adjustments to a process because of the instantaneous determination of the vapor pressure as compared to the above mentioned prior art. Another major benefit of the present invention is its ability to consistently give accurate and repeatable results.

Determination of the vapor pressure is achieved by directing a side stream flow of the liquid mixture whose vapor pressure is to be analyzed into the present invention. This sample stream is passed from the inlet valve 1 into a filter 3 to remove any solids that might plug the pressure reduction device 6. From the filter 3, the stream goes into a heater/cooler 4 to achieve the desired temperature at which the vapor pressure is to be determined. Another purpose of the heatedcooler 4 is to maintain a certain temperature to prevent precipitation of dissolved solids that could plug the apparatus. From the heate/cooler 4, the fluid passes to an upstream aeration measurement device 5 in FIG. 1 such as Controlotron's ultrasonic meter with % aeration measurement or upstream density measurement device 5a in FIG. 2 such as a vibrating tube type density meter. The upstream density device 5a will measure initial density of the sample. The upstream aeration measurement device 5 measures how much initial undissolved gas is contained in the sample. This initial measurement is the basis for determining when bubbling or initial flashing starts to occur. From the upstream density device 5a or aeration measurement device 5, the fluid passes through the pressure reduction device 6 shown as a capillary tubing, where the pressure of the liquid is smoothly reduced. A pressure reducing means that smoothly reduces the pressure, such as a capillary tubing, is selected to eliminate pressure recovery. A pressure control valve that forms a vena contracta can result in erroneous vapor pressures because upon pressure recovery at the point past the vena contracta, the bubbles formed initially in the vena contracta may not collapse back and would result in a higher vapor pressure measurement than what the true vapor pressure of the mixture is. As the pressure drops, the component of the mixture which has the highest vapor pressure starts to flash or effervesce. This point is the vapor pressure of the liquid mixture. At the outlet of the pressure reduction device 6 shown as capillary tubing, a pressure measurement device 7 is connected to measure the vapor pressure of the sample. A temperature measurement device 8 is also located at the same point to measure the temperature at which the vapor pressure is measured. The turbulence and liquid shear created as the sample passes through the pressure reduction means 6 reduces surface tension and promote flashing or creation of bubbles as soon as the vapor pressure is reached. This is in contrast to a stagnant sample, as described in the second mentioned prior art above, which is expanded in a cylinder to a pressure lower than the vapor pressure and then waiting for the pressure to reach equilibrium as the sample gradually flashes and reach some pressure corresponding to the expanded volume, such pressure not necessarily indicative of the true vapor pressure and may be affected by the surface tension of the sample.

Figure 2:
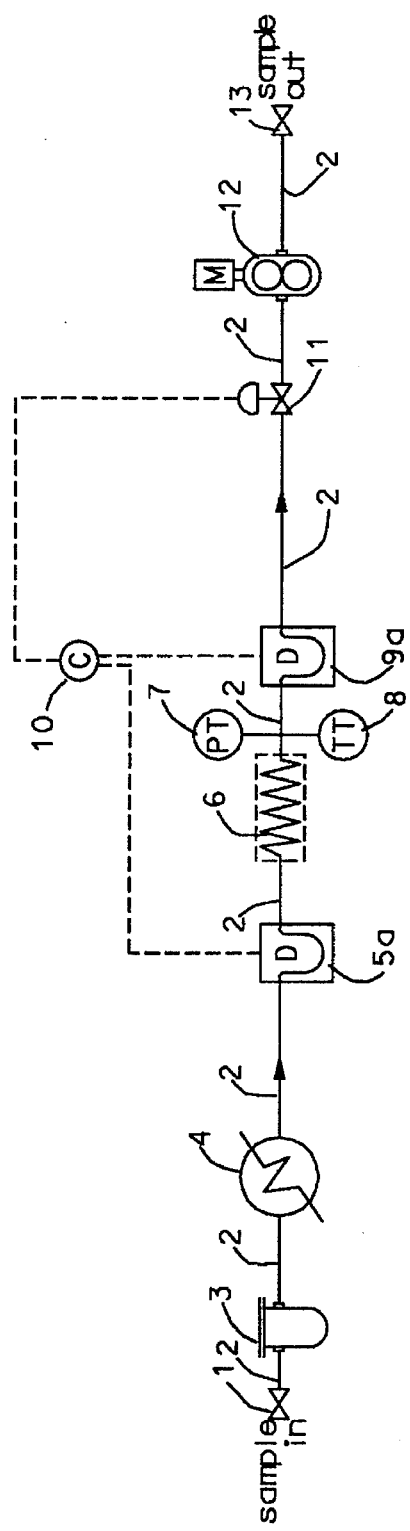
FIG. 2 is a schematic representation of the vapor pressure measurement apparatus according to the present invention showing density measurement means for detecting flashing or formation of bubbles.

From the pressure reduction means 6, the fluid passes to the downstream aeration measurement device 9 in FIG. 1 or the downstream density measurement device 9a in FIG. 2. The upstream and downstream device measurements are compared and a difference signal is sent to the flow controller 10. From the downstream density or aeration measurement device the sample passes to the flow control valve 11. The flow control valve 11 regulates the amount of sample that is admitted to the vapor pressure analyzer which in turn controls the amount of pressure drop in the capillary tubing. The flow control valve 11 is controlled by flow controller 10 which gets its signal from the difference signal of the upstream and downstream density or aeration measurements. A set difference in upstream and downstream aeration or density of the sample or a set downstream aeration measurement or a set downstream density will be the set point of the flow controller. The sample flow will be regulated such that the pressure drop through the capillary tubing is the minimum required to flash the lightest fraction of the liquid sample. The higher the flow through the capillary tubing the higher the pressure drop. From the flow control valve 11, the sample goes to the suction of the pump 12. The pump 12 boosts the pressure back to line pressure where the sample is returned to the main liquid stream. The discharge of the pump is connected to the return line through the outlet valve 13 at some point in the process line downstream of the sampling inlet tap. To maintain constant temperature of the sample, the components of the analyzer from the heater/cooler 4 up to the flow control valve 11 will be insulated. The various devices are interconnected using tubing 2. Those skilled in the art will recognize that other methods of decreasing the pressure or detecting the flashing or effervescence of the sample can be devised but such arrangements would not depart from the essential principles of this invention.

I claim:

1. A vapor pressure analyzer to determine the vapor pressure of single or multi component liquids comprising of an inlet conduit, a filter, a heating/cooling means to condition the single or multi component liquid, an upstream aeration measurement means to establish an aeration reference of the liquid, a capillary tubing pressure reduction means to decrease the pressure of the liquid smoothly to its vapor pressure oriented in a horizontal position or a pressure reducing valve which does not create pressure recovery nor a vena contracta, such vena contracta resulting in some pressure recovery and erroneous data, a downstream aeration measurement means that detects the minimum change in aeration compared to the upstream aeration measurement resulting from the pressure having reached the vapor pressure of the lightest component of the sample, a pressure measurement means to measure the actual vapor pressure at the point where the liquid starts to flash or effervesce, a temperature measurement means at the same location as the pressure measurement means, instrumentation and control means to control the liquid flow and therefore the pressure drop across the pressure reduction means at the desired condition that will result in the vapor pressure occurring at the point where the pressure measurement means is located, a pump to increase the liquid pressure back to system pressure to return the liquid back to the system at a point downstream of an extraction point, instrumentation means to process the difference in aeration between the sample upstream and downstream of the pressure reduction means, and flow tubing interconnecting the above mentioned devices.

2. A vapor pressure analyzer according to claim 1 containing instrument and control means to control the flow of the liquid admitted to the analyzer such that the pressure drop through the pressure reduction means is the minimum required to flash the fraction of the mixture having the highest vapor pressure as indicated by the minimum change in aeration that can be attributed to initial flashing or formation of bubbles in the sample as indicated by the difference between the upstream and downstream aeration measurement means.

3. A vapor pressure analyzer according to claim 1 containing downstream aeration measurement means such that the vapor pressure is obtained when the downstream aeration value reaches some pre-determined set point aeration value at the given temperature without having to compare with the upstream aeration measurement.

4. A vapor pressure analyzer according to claim 1 containing a capillary tubing pressure reduction means or a pressure reducing valve such that the turbulence and liquid shear created as the liquid passes through the pressure reduction means promote bubble formation or flashing at the actual vapor pressure of the liquid.

5. A vapor pressure analyzer to determine the vapor pressure of single or multi component liquids comprising of an inlet conduit, a filter, a heating/cooling means to condition the single or multi component liquid, an upstream density measurement means to establish density reference of the liquid, a capillary tubing pressure reduction means to decrease the pressure of the liquid smoothly for pressure reduction and oriented in a horizontal position or a pressure reducing valve which does not create pressure recovery nor a vena contracta, such vena contracta resulting in some pressure recovery and erroneous data, a downstream density measurement means that detects the minimum change in density compared to the upstream density measurement resulting from the pressure having reached the vapor pressure of the lightest component of the sample, a pressure measurement means to measure the actual vapor pressure at the point where the liquid starts to flash or effervesce, a temperature measurement means at the same location as the pressure measurement means, instrumentation and control means to control the liquid flow and therefore the pressure drop across the pressure reduction means at the desired condition that will result in the vapor pressure occurring at the point where the pressure measurement means is located, a pump to increase the sample pressure back to system pressure to return the liquid back to the system at a point downstream of an extraction point, instrumentation means to process the difference in density between the sample upstream and downstream of the pressure reduction means, and flow tubing interconnecting the above mentioned devices.

6. A vapor pressure analyzer according to claim 5 containing instrument and control means to control the flow of the sample admitted to the analyzer such that the pressure drop through the pressure reduction means is the minimum required to flash the fraction of the mixture having the highest vapor pressure as indicated by the minimum change in density that can be attributed to initial flashing or formation of bubbles in the sample and not merely to change in density caused by expansion of liquid due to drop in pressure.

7. A vapor pressure analyzer according to claim 5 containing downstream density measurement means such that the vapor pressure is obtained when the downstream density value reaches some pre-determined set point density value at the given temperature without having to compare with the upstream density measurement.

8. A vapor pressure analyzer according to claim 5 containing a capillary tubing pressure reduction means or a pressure reducing valve such that the turbulence and liquid shear created as the sample passes through the pressure reduction means promote bubble formation or flashing at the actual vapor pressure of the liquid.

\* \* \* \* \*